(12) United States Patent
Chang et al.

(10) Patent No.: US 9,580,394 B2
(45) Date of Patent: Feb. 28, 2017

(54) BENZODIAZEPINE DERIVATIVE AND METHOD OF PRODUCING THE SAME

(71) Applicant: ATOMIC ENERGY COUNCIL-INSTITUTE OF NUCLEAR ENERGY RESEARCH, Taoyuan County (TW)

(72) Inventors: Yu Chang, Taoyuan County (TW); Ching-Yun Lee, Taoyuan County (TW); Tsung-Hsien Chiang, Taoyuan County (TW); Cheng-Fang Hsu, Taoyuan County (TW)

(73) Assignee: Atomic Energy Council—Institute of Nuclear Energy Research, Taoyuan County (TW)

( * ) Notice: Subject to any disclaimer, the term of this patent is extended or adjusted under 35 U.S.C. 154(b) by 0 days.

(21) Appl. No.: 14/200,393

(22) Filed: Mar. 7, 2014

(65) Prior Publication Data
US 2015/0252009 A1    Sep. 10, 2015

(51) Int. Cl.
*C07D 243/14*    (2006.01)
*C07D 243/12*    (2006.01)

(52) U.S. Cl.
CPC .................................. *C07D 243/12* (2013.01)

(58) Field of Classification Search
CPC ...................................................... C07D 243/14
See application file for complete search history.

(56) References Cited

U.S. PATENT DOCUMENTS 6,458,783 B1 * 10/2002 Ding et al. .................... 514/220

\* cited by examiner

*Primary Examiner* — Bruck Kifle
(74) *Attorney, Agent, or Firm* — Rosenberg, Klein & Lee

(57) ABSTRACT

In a benzodiazepine derivative and a method of producing the derivative, isatoic anhydride or 5-chloroisatoic anhydride is reacted with amino acid ester hydrochloride for conducting a simple cyclization to obtain a produce with a low percentage of by-product directly without requiring the complicated separation and purification processes of column chromatography, and a chlorine-containing structure of the structure can improve the lipo-solubility and chlorine ion permeability and allow a functional group of a radioisotope to be modified to maximize the effects of the pharmacological properties such as the sedative, anticonvulsant and anti-spasmodic effects on the central nervous system or the benzodiazepine derivative can be used as a contrast agent of the system with excellent effects on applications.

10 Claims, 6 Drawing Sheets

(1A)  (4)  (5A)

(1B)  (4)  (5B)

BENZODIAZEPINE DERIVATIVE AND METHOD OF PRODUCING THE SAME

FIELD OF THE INVENTION

The present invention relates to a derivative and a method of producing the same, and more particularly to a benzodiazepine derivative and a method of producing the benzodiazepine derivative by reacting an isatoic anhydride or 5-chloroisatoic anhydride with amino acid ester hydrochloride to accomplish a simple synthesis with good effects.

BACKGROUND OF THE INVENTION

Flumazenil is an antagonist of a benzodiazepine receptor of a brain, and benzodiazepine is a sedative-hypnotic drug that plays an important role in the central nervous system of the brain, and benzodiazepine has been used extensively in the medical field since 1960 and clinically used for treating anxiety disorder, insomnia, alcohol withdrawal syndrome, etc.

Gamma-Aminobutyric Acid (GABA) is recently discovered major inhibitory neurotransmitter capable of relieving or suppressing excessive excitement and intense nerve signal transmission to calm people down. GABA receptors are distributed extensively in cerebral cortex, and some of the GABA receptors have chloride ion channels, and these GABA receptors are benzodiazepine. The benzodiazepine receptors of this sort can be used for tracking a radioactive flumazenil derivative and pointing out the position of epilepsy more sensitively and accurately than [$^{18}$F]FDG.

The so-called antagonist refers to a drug that can substitute benzodiazepine to combine with a receptor, so as to suppress related central nervous system activities of the bran and achieve a sedative, anticonvulsant or antiepileptic effect. The substitution simulates the active site of the benzodiazepine and provides a better affinity to enhance the structural basis of being the antagonist.

As to the structure of flumazenil, 1,4-benzodiazepine-2, 5-dione acts as the basic structure, and this structure may be a benzodiazepine receptor antagonist, and thus it is a valuable research subject to produce a related derivative by a simple method and improve the performance by an appropriate structural modification.

In a conventional method of synthesizing a benzodiazepine derivative, isatoic anhydride and an amino acid are dissolved in dimethyl sulfoxide (DMSO) and then heated to perform a reaction and produce a crude product. After the crude product is pre-treated by neutralization and extraction, a column chromatography process is provided to elute and purify the crude product by ethyl acetate ethanol in an appropriate ratio, and finally a cyclized product is obtained.

However, the boiling point and polarity of DMSO are very high, so that the DMSO cannot be removed easily by simple evaporation or extraction, and a portion of DMSO together with the crude product goes through the column chromatography process. The quantity of the crude product increases with the DMSO, and thus the quantity of static phased filling becomes greater and the elution time becomes longer in the column chromatography process, and the chromatographed product is often an oily substance without a fixed shape. In the meantime, it is unable to find a suitable solvent for the re-crystallization to set the fixed shape of a solid. Regardless of the reaction conditions and the separation and purification methods, it is necessary to find a more appropriate process.

Therefore, it is a main technical issue for the present invention to provide a novel synthesis method to produce a benzodiazepine derivative in an easy and convenient manner and allow the structure to have a specific modification to increase the application value.

SUMMARY OF THE INVENTION

It is a primary objective of the present invention to provide a benzodiazepine derivative with a fixed crystalline white solid which is also a compound with stable chemical properties and convenient storage. For a re-purification, it simply requires washing the derivative with an appropriate solvent or re-crystallizing it to the original fixed crystal, and the high stability is conducive to commercial applications and promotions.

Another objective of the present invention is to provide a benzodiazepine derivative whose structure is further grafted with a functional group containing a radioisotope, and such modified benzodiazepine derivative can be used for exploring the diagnostic functions of the central nervous system diseases of the brain and maximizing the effect of radiography.

A further objective of the present invention is to provide a benzodiazepine derivative whose structure is added with chlorine atoms to achieve the effect of improving the liposolubility and chlorine ion permeability and expecting to enhance the pharmacological properties such as the sedative, anticonvulsant and anti-spasmodic effects in the central nervous system.

Another objective of the present invention is to provide a method of producing a benzodiazepine derivative with a low percentage of by-products, so that an appropriate solvent can be found, and a cyclized product can be produced by a simple re-crystallization method without requiring a long column chromatography process to elute the product, so as to reduce the time and cost of the production significantly.

To achieve the aforementioned objectives, the present invention provides a benzodiazepine derivative and a method of producing the same, and the method comprises the steps of: dissolving isatoic anhydride and amino acid ester hydrochloride into a solvent to produce a reaction solution; heating and refluxing the reaction solution; cooling the temperature of the reaction solution to room temperature and then acidifying the reaction solution; extracting the reaction solution, and washing the reaction solution with salt water and drying and filtering the reaction solution to obtain a crude product; and re-crystallizing the crude product to obtain the benzodiazepine derivative; wherein the amino acid ester hydrochloride is one selected from a group consisting of glycine methyl ester hydrochloride, L-aspartic acid dimethyl ester hydrochloride and L-aspartic acid dibenzyl ester p-toluenesulfonate salt. Based on the aforementioned method, a benzodiazepine derivative with a better pharmacological effect for the central nervous system of the brain can be produced simply and easily.

DESCRIPTION OF THE PREFERRED EMBODIMENTS

The technical characteristics of the present invention will become clearer in light of the following detailed description of illustrative preferred embodiments of this invention. It is intended that the preferred embodiments disclosed herein are to be considered illustrative rather than restrictive.

Figure 1:
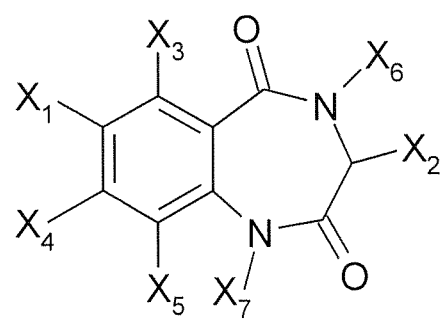
FIG. 1 shows the chemical structure of a benzodiazepine derivative of the invention.

With reference to FIG. 1 for the chemical structure of a benzodiazepine derivative of the invention, different substances can be selected as a reactant for the synthesis process to obtain benzodiazepine derivatives with different functional groups $X_1$ to $X_7$, wherein $X_1$ is a hydrogen or chlorine group, $X_2$ is a hydrogen group, methyl formate or benzyl acetate, and $X_3$ to $X_7$ is connected to a functional group having a radioisotope as a modification for applications, so that the benzodiazepine derivative can be used as a contrast agent.

In these derivatives with the structure of using benzodiazepine as a common core and different functional groups for modification, the lipo-solubility and chlorine ion permeability can be improved appropriately to provide sufficient pharmacological properties to the central nervous system for the sedative, anticonvulsant or antiepileptic effect, if chlorine is used as the substituting group in a six-membered benzene ring, As to the seven-membered ring, the ring is connected to a structure coming from amino acid ester hydrochloride, since when the benzodiazepine derivative of the present invention is produced, the relatively stable amino acid ester hydrochloride is used as a reactant to achieve a more stable effect than simply using an amino acid. Therefore, a lower percentage of by-products can be achieved, and the time-consuming column chromatography process for eluting the product can be waived to simplify the complexity of the production process.

Figure 2:
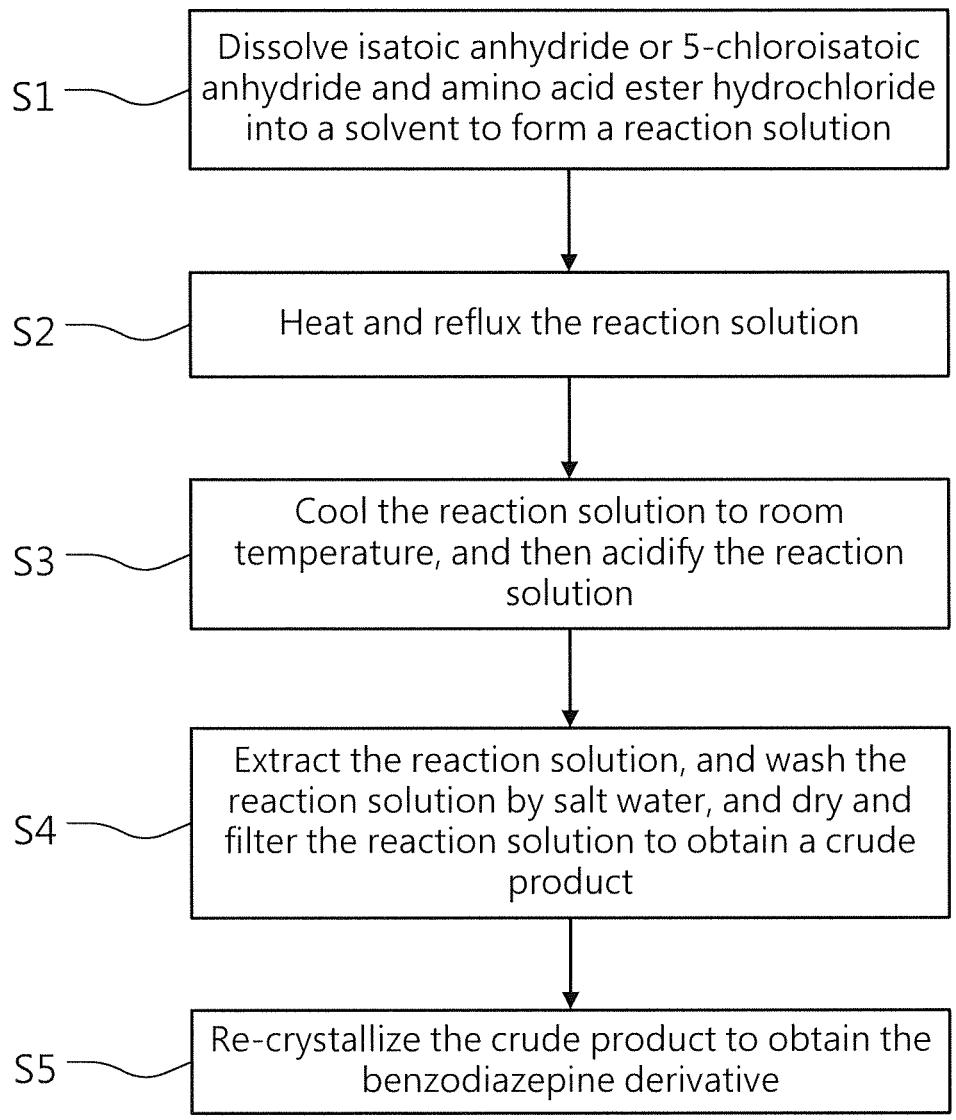
FIG. 2 is a flow chart of a method of producing a benzodiazepine derivative of the invention.

With reference to FIG. 2 for a flow chart of a method of the present invention, the method comprises the following steps S1: Dissolve isatoic anhydride or 5-chloroisatoic anhydride and amino acid ester hydrochloride into a solvent to form a reaction solution.

S2: Heat and reflux the reaction solution.

S3: Cool the reaction solution to room temperature, and then acidify the reaction solution.

S4: Extract the reaction solution, and wash the reaction solution by salt water, and dry and filter the reaction solution to obtain a crude product.

S5: Re-crystallize the crude product to obtain the benzodiazepine derivative.

The method of the present invention is intended for reducing the production of the crude product, so that the complicated separation and purification processes of column chromatography can be waived, and the benzodiazepine derivative with good pharmacological properties such as the sedative, anticonvulsant and anti-spasmodic effects can be obtained. In addition, the method also can improve the production rate significantly.

Figure 3A:
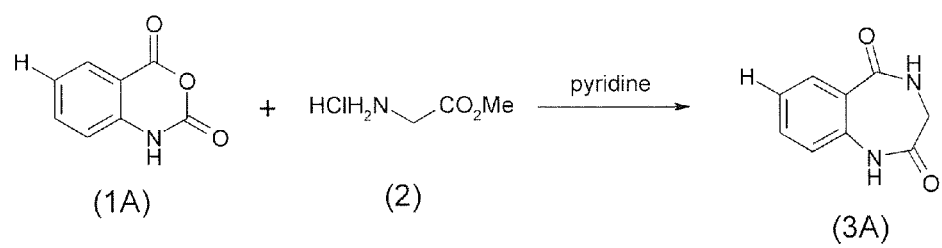
FIGS. 3A and 3B show the chemical reaction formula of using glycine methyl ester hydrochloride as a reactant of the invention.

In the present invention, isatoic anhydride or 5-chloroisatoic anhydride is used as a reaction initiator. For example, isatoic anhydride (compound 1A) and glycine methyl ester hydrochloride (compound 2) are dissolved into a solvent (pyridine) as shown in the chemical reaction of FIG. 3A. In the reaction, the aforementioned steps S2~S5 take place to obtain the final product 2,5-Dioxo-2,3,4,5-tetrahydro-1H-1,4-benzodiazepine (compound 3A) which is one of the benzodiazepine derivatives.

Figure 3B:
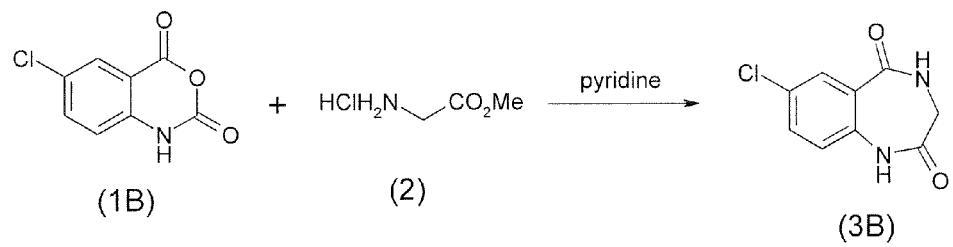

To improve the lipo-solubility and chlorine ion permeability of the benzodiazepine derivative appropriately to maximize the pharmacological properties of the benzodiazepine derivative, 5-chloroisatoic anhydride also can be used as the reaction initiator in the same operation conditions. In FIG. 3B, 5-chloroisatoic anhydride (compound 1B) and glycine methyl ester hydrochloride (compound 2) are dissolved into a solvent (pyridine). In the reaction, the final product 7-chloro-2,5-dioxo-2,3,4,5-tetrahydro-1H-1,4-benzodiazepine (compound 3B) is formed.

The present invention uses amino acid ester hydrochloride as the substance to react with isatoic anhydride or 5-chloroisatoic anhydride, since amino acid ester hydrochloride has stable chemical properties, convenient-to-store feature and good reactivity. Besides the aforementioned glycine methyl ester hydrochloride, L-aspartic acid dimethyl ester hydrochloride and L-aspartic acid dibenzyl ester p-toluenesulfonate salt can be also used selectively.

Figure 4A:
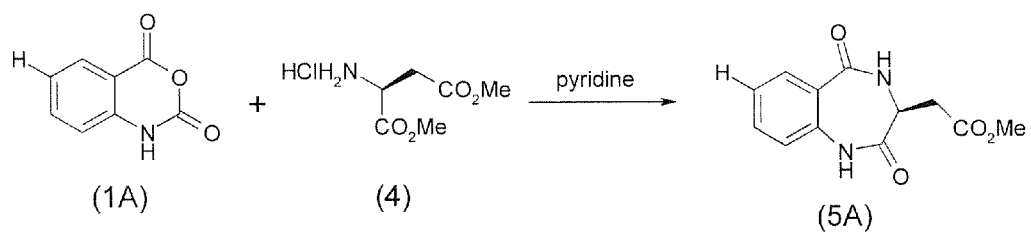
FIGS. 4A and 4B show the chemical reaction formula of using L-aspartic acid dimethyl ester hydrochloride as a reactant of the invention.
Figure 4B:
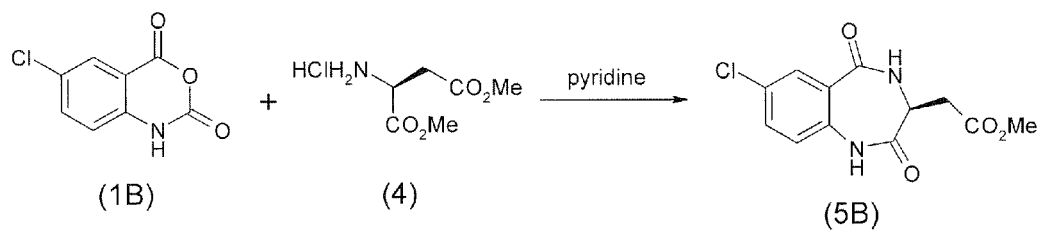

In FIGS. 4A and 4B, L-aspartic acid dimethyl ester hydrochloride (compound 4) is reacted with isatoic anhydride (compound 1A) and 5-chloroisatoic anhydride (compound 1B) to form 2,5-dioxo-2,3,4,5-tetrahydro-1H-1,4-benzodiazepine-3-acetic acid methyl ester (compound 5A) and 7-chloro-2,5-dioxo-2,3,4,5-tetrahydro-1H-1,4-benzodiazepine-3-acetic acid ethyl ester (compound 5B).

Figure 5A:
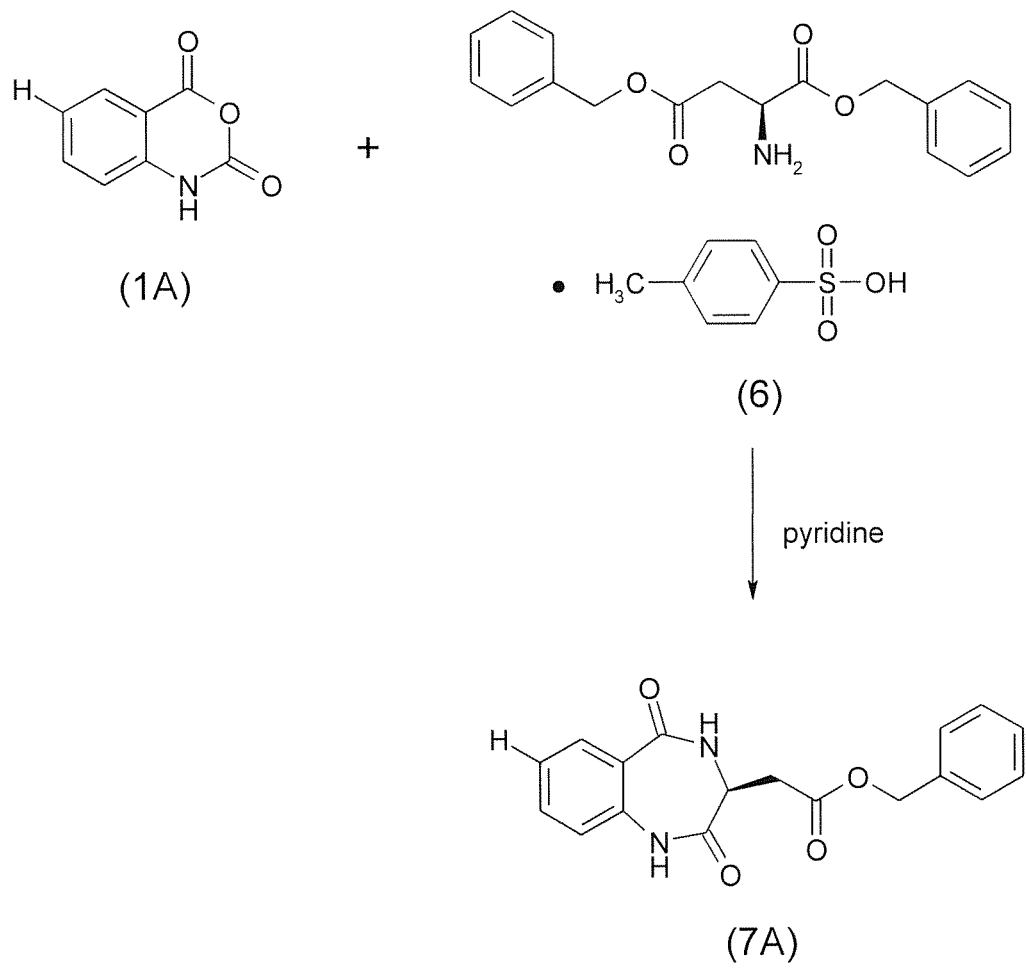
FIGS. 5A and 5B show the chemical reaction formula of using L-aspartic acid dibenzyl ester p-toluenesulfonate as a reactant of the invention.
Figure 5B:
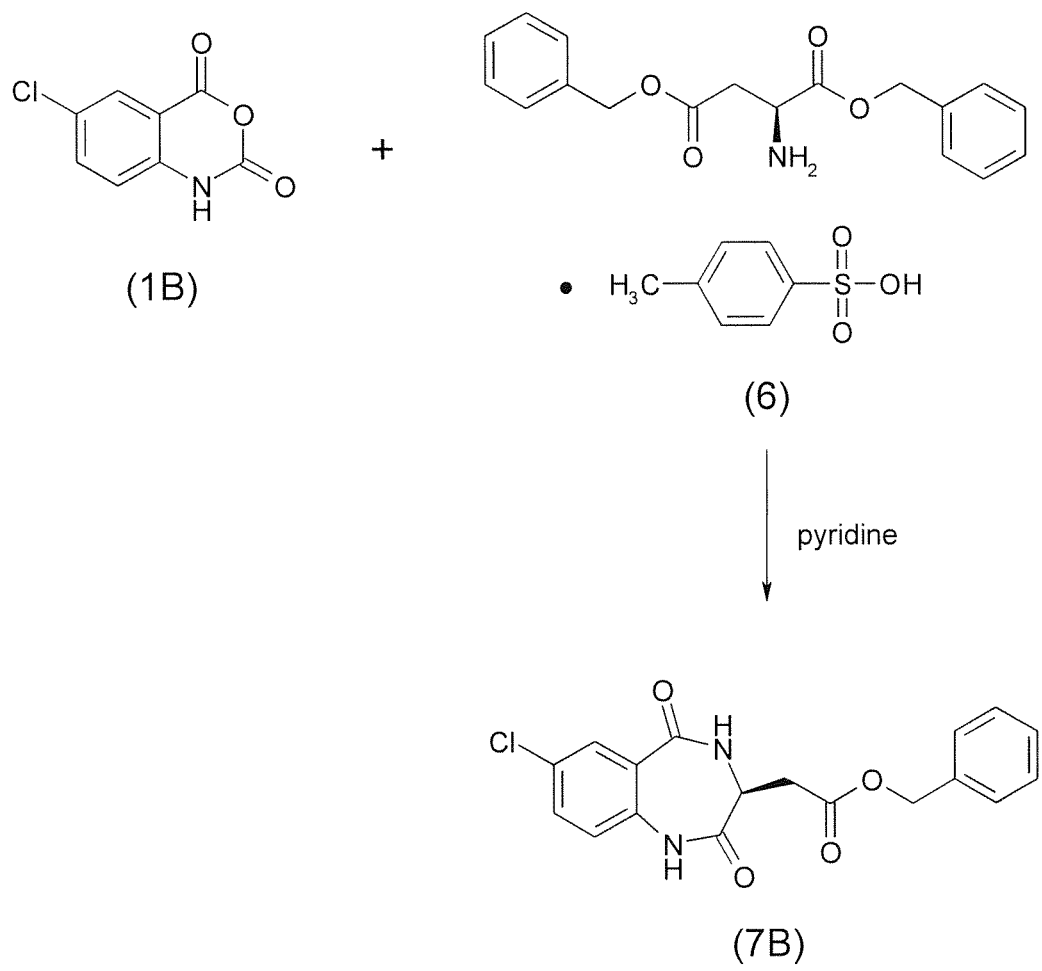

In FIGS. 5A and 5B, L-aspartic acid dibenzyl ester p-toluenesulfonate salt (compound 6) is reacted with isatoic anhydride (compound 1A) and 5-chloroisatoic anhydride (compound 1B) to form 2,5-Dioxo-2,3,4,5-tetrahydro-1H-1,4-benzodiazepine-3-acetic acid benzyl ester (compound 7A) and 7-chloro-2,5-dioxo-2,3,4,5-tetrahydro-1H-1,4-benzodiazepine-3-acetic acid benzyl ester (compound 7B) respectively.

With reference to the molecular structure of the benzodiazepine derivative as shown in FIG. 1, $X_1$ can be a hydrogen group or a chlorine group since the reactant is isatoic anhydride or 5-chloroisatoic anhydride. If a different reactant (amino acid ester hydrochloride), $X_2$ can be a hydrogen group, methyl acetate or benzyl acetate.

During the production process of the present invention, after amino acid ester hydrochloride and isatoic anhydride, or 5-chloroisatoic anhydride are dissolved into pyridine to form a chemical solution, the chemical solution is heated and refluxed to have a sufficient reaction within a temperature range of 110~120° C. and the reaction time is preferably equal to 18 hours. After a complete reaction takes place, the reaction solution is cooled to room temperature, and then 6N HCl is added into the reaction solution to adjust the pH value of the reaction solution to a range of 0.8~1.2, so that the reaction solution is acidified. Preferably, the pH value is adjusted to 1.

And then, ethyl acetate is used as a solvent for extracting the acidified reaction solution. After the combined organic layer is washed by salt water, and then anhydrous magnesium sulfate is used as a water absorbent for drying the chemical solution, and the chemical solution is filtered to obtain a crude product. The solvent of the crude product is further evaporated by a rotary evaporator to concentrate the crude product.

In the re-crystallization of step S5, water or ethyl acetate at room temperature is added, so that the crude product is suspended in water or ethyl acetate, and then heated to a temperature until the crude product is dissolved completely, and then the completely dissolved crude product solution is moved to a ventilation hood and cooled to room temperature to produce a solid benzodiazepine derivative of the present invention.

In the aforementioned operation, the percentage of by-products is very low, so that an appropriate solvent can be found to produce a cyclized product by a simple re-crystallization method without requiring the time consuming column chromatography to elute the product. In addition, the obtained benzodiazepine derivative is a fixed crystalline white solid product as well as a compound with the stable chemical properties and a convenient-to-store feature. If purification is required, an appropriate solvent can be used for washing the derivate and re-crystallize the derivate to the original fixed crystal.

The structure of the benzodiazepine derivative as disclosed in the present invention comprises a benzene ring and a seven-membered ring, wherein nitrogen atoms of the seven-membered ring are connected to the hydrogen group after the aforementioned production process takes place, and the nitrogen atoms can be grafted an appropriate branched chain for labeling a radioisotope $^{18}F$. In other words, $X_6$ and $X_7$ are functional groups including a radioisotope $^{18}F$. The six-membered benzene ring can be connected to a radioisotope $^{123}I$. In other words, $X_3$, $X_4$ and $X_5$ are functional groups including a radioisotope $^{123}I$. With the labeled appropriate radioisotope, the benzodiazepine derivative maximizes the effect of chromatography for diagnosing the central nervous system of a brain.

The data and detailed procedure of the actual operation of the method during the production in accordance with the present invention are listed below:

Synthesis of Compound 3A

Isatoic anhydride (compound 1A) (1 g, 6.13 mmol) and glycine methyl ester hydrochloride (compound 2) (0.77 g, 6.13 mmol) are dissolved into pyridine to form a chemical solution, and the chemical solution is heated to 120° C. and reacted for 18 hours. After 18 hours, the reaction solution is cooled to room temperature and drops of 6N HCl are added gradually to acidify the reaction solution to a pH value equal to 1. The acidified reaction solution is extracted by ethyl acetate, and an organic layer is combined, and the salts are removed by saturated salt water, and then anhydrous magnesium sulfate is used for drying and filtering. The filtered solution is concentrated to produce a crude product, and then the crude product is re-crystallized by water to obtain the final white solid product which is compound 3A (0.62 g, 56%).

Analysis Data of Compound 3A $^1$H-NMR (300 MHz, DMSO-$d_6$): δ 3.65 (dd, 1H), 7.17 (d, 1H), 7.28 (dd, 1H), 7.56 (dd, 1H), 7.82 (dd, 1H), 8.59 (dd, 1H), 10.4 (s, NH); $^{13}$C-NMR (75 MHz, DMSO-$d_6$): δ 171.6, 168.5, 137.6, 132.7, 131.2, 126.0, 124.3, 121.4, 44.9

Synthesis of Compound 3B 5-chloroisatoic anhydride (compound 1B) (1 g, 5.06 mmol) and glycine methyl ester hydrochloride (compound 2) (0.77 g, 6.13 mmol) are suspended in pyridine (20 mL) to form a suspended solution, and the suspended solution is heated to 110° C. and dissolved completely, and then reacted for 18 hours. After 18 hours, the reaction solution is cooled to room temperature, and drops of 6N HCl are added gradually to acidify the reaction solution to a pH value approximately equal to 1. The acidified reaction solution is extracted by ethyl acetate (50 mL×3), and the combined organic layer is washed by saturated salt water, and then anhydrous magnesium sulfate is used for drying and filtering. The filtered solution is concentrated to produce a crude product, and the crude product is re-crystallized by water to obtain the final white solid product which is the compound 3B (0.67 g, 63%).

Analysis Data of Compound 3B $^1$H-NMR (300 MHz, DMSO-$d_6$): δ 3.63 (dd, 1H), 7.15 (d, 1H), 7.58 (dd, 1H), 7.70 (dd, 1H), 8.65 (dd, 1H), 10.4 (s, NH); $^{13}$C-NMR (75 MHz, DMSO-$d_6$): δ 171.3, 167.2, 136.6, 132.5, 130.4, 128.3, 127.5, 123.4, 44.8

Synthesis of Compound 5A

Isatoic anhydride (compound 1A) (1 g, 6.13 mmol) and L-aspartic acid dimethyl ester hydrochloride (compound 4) (1.21 g, 6.13 mmol) are dissolved in pyridine to produce a chemical solution, and the chemical solution is heated to 120° C. and reacted for 18 hours. After 18 hours, the reaction solution is cooled to room temperature, and drops of 6N HCl are added gradually to acidify the reaction solution to a pH value of 1. The acidified reaction solution is extracted by ethyl acetate, and the combined organic layer is saturated by saturated salt water to remove the salts, and anhydrous magnesium sulfate is used for drying and filtering. The filtered solution is concentrated to produce a crude product, and then the crude product is re-crystallized by ethyl acetate and water to produce the final white solid product which is the compound 5A (0.46 g, 30%).

Analysis Data of Compound 5A $^1$H-NMR (300 MHz, DMSO-$d_6$): δ 2.71 (dd, 1H), 2.86 (dd, 1H), 3.57 (s, 3H), 4.06 (ddd, 1H), 7.10 (d, 1H), 7.23 (dd, 1H), 7.52 (dd, 7.74 (dd, 1H), 8.57 (dd, 1H), 10.4 (s, NH); $^{13}$C-NMR (75 MHz, DMSO-$d_6$): δ 171.1, 171.0, 168.1, 137.0, 132.8, 130.9, 126.7, 124.6, 121.5, 52.0, 49.0, 32.0

Synthesis of Compound 5B 5-chloroisatoic anhydride (compound 1B) (1 g, 5.06 mmol) and L-aspartic acid dimethyl ester hydrochloride (compound 4) (1.21 g, 6.13 mmol) are suspended in pyridine (20 mL), and the suspended solution is heated to 120° C. and dissolved completely, and reacted for 18 hours. After 18 hours, the reaction solution is cooled to room temperature, and drops of 6N HCl are added gradually to acidify the reaction solution to a pH value approximately equal to 1. The acidified reaction solution is extracted by ethyl acetate (50 mL×3), and the combined organic layer is washed by saturated salt water, and then anhydrous magnesium sulfate is used for drying and filtering. The filtered solution is concentrated to produce a crude product, and the crude product is re-crystallized by ethyl acetate and water to produce the final white solid product which is the compound 5B (0.46 g, 32.2%).

Analysis Data of Compound 5B $^1$H-NMR (300 MHz, DMSO-$d_6$): δ 2.71 (dd, 1H), 2.86 (dd, 1H), 3.60 (s, 3H), 4.05 (ddd, 1H), 7.12 (d, 1H), 7.60 (dd, 1H), 7.70 (d, 1H), 8.70 (dd, 1H), 10.58 (s, NH); $^{13}$C-NMR (75 MHz, DMSO-$d_6$): δ 171.9, 171.0, 166.1, 136.0, 132.7, 130.2, 128.7, 128.1, 123.5, 52.0, 49.0, 33.0

Synthesis of Compound 7A

Isatoic anhydride (compound 1A) (1 g, 6.13 mmol) and L-aspartic acid dibenzyl ester p-toluenesulfonate salt (compound 6) (1 g, 6.13 mmol) are dissolved in pyridine to form a chemical solution, and the chemical solution is heated to 120° C. and reacted for 18 hours. After 18 hours, the reaction solution is cooled to room temperature, and drops of 6N HCl are added gradually to acidify the reaction solution to a pH value of 1. The acidified reaction solution is extracted by ethyl acetate, and the combined organic layer is washed by saturated salt water to remove the salts, and then anhydrous magnesium sulfate is used for drying and filtering. The filtered solution is concentrated to form a crude product, and the crude product is re-crystallized by ethyl acetate and water to obtain the final white solid product which is the compound 7A (0.36 g, 18%).

Analysis Data of Compound 7A $^1$H-NMR (300 MHz, DMSO-$d_6$): δ 2.78 (dd, 1H), 2.90 (dd, 1H), 4.07 (ddd, 1H), 5.07 (s, 2H), 7.10 (d, 1H), 7.27 (dd, 1H), 7.33 (m, 5H), 7.75 (dd, 1H), 8.62 (dd, 1H), 10.4 (s, NH); $^{13}$C-NMR (75 MHz, DMSO-$d_6$): δ 171.3, 170.4, 168.1, 137.0, 136.4, 132.8, 130.9, 128.8, 128.4, 128.1, 126.7, 124.7, 121.5, 66.0, 49.1, 33.1

Synthesis of Compound 7B 5-chloroisatoic anhydride (compound 1B) (1 g, 5.06 mmol) and L-aspartic acid dibenzyl ester p-toluenesulfonate salt (6) (2.98 g, 6.13 mmol) are suspended in pyridine (20 mL) to form a suspended solution, and the suspended solution is heated to 120° C. and dissolved completely and reacted for 18 hours. After 18 hours, the reaction solution is cooled to room temperature, and drops of 6N HCl are added gradually to acidify the reaction solution to a pH value approximately equal to 1. The acidified reaction solution is extracted by ethyl acetate (50 mL×3), and the combined organic layer is washed by saturated salt water, and then anhydrous magnesium sulfate is used for drying and filtering. The filtered solution is concentrated to obtain a crude product, and then the crude product is re-crystallized by ethyl acetate and water to obtain the final white solid product which is the compound 7B (0.36 g, 19.8%).

Analysis Data of Compound 7B $^1$H-NMR (300 MHz, DMSO-$d_6$): δ 2.80 (dd, 1H), 2.95 (dd, 1H), 4.10 (ddd, 1H), 5.05 (s, 2H), 7.10 (d, 1H), 7.33 (m, 5H), 7.60 (dd, 1H), 7.70 (d, 1H), 8.76 (dd, 1H), 10.60 (s, NH); $^{13}$C-NMR (75 MHz, DMSO-$d_6$): δ 171.0, 170.3, 166.1, 136.4, 135.9, 132.7, 130.2, 129.0, 128.7, 128.4, 128.2, 128.1, 121.6, 66.0, 49.0, 33.0

In summation of the description above, the present invention discloses a benzodiazepine derivative and a method of producing the same, and uses a simple cyclization to obtain a product with a low percentage of by-products directly without requiring the complicated separation and purification processes of column chromatography. In addition, the present invention uses amino acid ester hydrochloride as a reactant, and amino acid ester hydrochloride has stable chemical properties, convenient-to-store feature, and excellent reactivity which are necessary elements for an effective mass production of the benzodiazepine derivative. Further, the chlorine-containing structure of the present invention provides better lipo-solubility and ion permeability, and allows further grafting to the radioisotope to maximize the, the pharmacological properties such as the sedative, anti-convulsant and anti-spasmodic effects on the central nervous system, or the derivative can be used as a contrast agent to achieve excellent effects. Overall speaking, the present invention achieves excellent production efficiency and product performance, and undoubtedly provides a benzodiazepine derivative and a method of producing the same with economic values.

What is claimed is:

1. A method of producing a compound of the following formula A

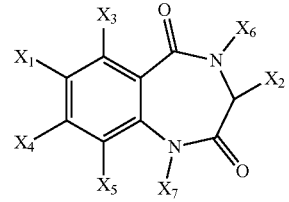

formula A wherein, $X_1$ is one selected from the hydrogen group, $X_2$ is one selected from the group consisting of a hydrogen group, a methoxycarbonyl group and a benzyloxycarbonyl group, and $X_3$, $X_4$, $X_5$, $X_6$ and $X_7$ are all hydrogen group comprising the steps of;
dissolving isatoic anhydride and L-aspartic acid dimethyl ester hydrochloride into a solvent to form a reaction solution;
heating and refluxing the reaction solution;
cooling the reaction solution to room temperature, and then adds HCl into the reaction solution to adjust the pH value to a range of 0.8~1.2;
extracting the reaction solution, washing the reaction solution by salt water, and drying and filtering the reaction solution to obtain a crude product; and
re-crystallizing the crude product to obtain the compound of formula A.

2. The method of claim 1, wherein the solvent is pyridine.

3. The method of claim 1, wherein the step of heating and refluxing the reaction solution heats the reaction solution to a temperature falling within a range of 110~120° C. for 18 hours.

4. The method of claim 1, wherein the step of extracting the reaction solution uses ethyl acetate as the solvent.

5. The method of claim 1, wherein the step of drying the reaction solution adds anhydrous magnesium sulfate into the reaction solution.

6. A method of producing a compound of the following formula A'

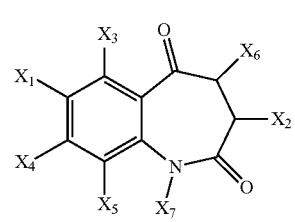

formula A' wherein, $X_1$ is selected from the chlorine group, $X_2$ is one selected from the group consisting of a hydrogen group, a methoxycarbonyl group and a benzyloxycarbonyl group, and $X_3$, $X_4$, $X_5$, $X_6$ and $X_7$ are all hydrogen group, comprising the steps of:
dissolving 5-chloroisatoic anhydride and amino acid ester hydrochloride into a solvent to form a reaction solution;
heating and refluxing the reaction solution;
cooling the reaction solution to room temperature, and then adds HCl into the reaction solution to adjust the pH value to a range of 0.8~1.2;
extracting the reaction solution, washing the reaction solution by salt water, and drying and filtering the reaction solution to obtain a crude product; and re-crystallizing the crude product to obtain the compound of formula A.

7. The method of claim 6, wherein the solvent is pyridine.

8. The method of claim 6, wherein the step of heating and refluxing the reaction solution heats the reaction solution to a temperature falling within a range of 110~120° C. for 18 hours.

9. The method of claim 6, wherein the step of extracting the reaction solution uses ethyl acetate as the solvent.

10. The method of claim 6, wherein the step of drying the reaction solution adds anhydrous magnesium sulfate into the reaction solution.

* * * * *